US00PP31824P3

(12) United States Plant Patent
Maillard et al.

(10) Patent No.: US PP31,824 P3
(45) Date of Patent: Jun. 2, 2020

(54) CHERRY TREE NAMED 'PINKILAM'

(50) Latin Name: ***Prunus avium* (L.) L.**
Varietal Denomination: PINKILAM

(71) Applicant: AGRO SELECTIONS FRUITS, Elne (FR)

(72) Inventors: Arsène Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 16/350,458

(22) Filed: Nov. 20, 2018

(65) Prior Publication Data

US 2019/0159379 P1 May 23, 2019

(30) Foreign Application Priority Data

Nov. 23, 2017 (QZ) ..... PBR 2017/3043

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/08; A01H 5/085; A01H 5/0216; A01H 5/0837; A01H 6/74; A01H 6/7445
See application file for complete search history.

*Primary Examiner* — June Hwu
(74) *Attorney, Agent, or Firm* — Birch, Stewart, Kolasch & Birch, LLP

(57) ABSTRACT

A new and distinct variety of cherry tree denominated 'PINKILAM' has fruits with precocious and important fruit set, that ripen early in the season, with large size and two-colored fruit skin, very firm, and with a very good and semi-sweet flavor and eating quality; the fruit is further characterized by its good handling and storage qualities.

4 Drawing Sheets

Latin name of the genus and species of the plant claimed: *Prunus avium* (L.) L.

Variety denomination: 'PINKILAM'.

This application claims priority of Community plant variety right No. 2017/3043 filed on Nov. 23, 2017 which is hereby incorporated by reference in its entirety.

The new variety named 'PINKILAM' is also known as 02.15.06.09 CE-ASF0904. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and the year of selection. Then before being named 'PINKILAM', the provisional reference of this cherry tree variety was 02.15.06.09CE, corresponding to the tree 6 located in line 15 of the parcel 2 and selected during the year 2009. The letters "CE" are related to the first letters of the type of tree in French (CE for "CErise", that means "cherry"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'PINKILAM', the clone reference was 'ASF0904.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary.

It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'PINKILAM'. This tree produces fruits with a long shelf life without alteration both on the trees after growth completion and after harvesting, very good eating quality with a cream yellow colored flesh, and for fresh market from mid-May to the end of May in the Pyrénées Orientales department, France.

Contrast is made to 'RUBILAM' cherry tree (U.S. Plant Pat. No. 23,798), 'ROSALOLAM' cherry tree (U.S. Plant Pat. No. 29,252), 'BURLAT' cherry tree (not patented), and 'FOLFER' (not patented) cherry tree for reliable description. 'PINKILAM' is a promising candidate for commercial success in that it produces very attractive fruits having a long shelf life.

The present new variety of cherry tree (*Prunus avium* L.) was developed by us in our experimental orchard located in France. 'PINKILAM' cherry tree originated in a cultivated area of the South of France, in the Pyrénées-Orientales department where it was also tested. This zone also called Roussillon is subject to a Mediterranean climate. The winter is generally sweet that is to say the total amount of cold hours lower than 7° C. (Celsius) varies from 600 hours to 1200 hours. The summer is hot and dry, that is to say the total amount of sunshine hours is an average of 2400 hours to 2800 hours per year. The prevailing wind is called "Tramontane": it dries the air and clear the sky from clouds, but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen, and the summer is dry with a few thunderstorms.

The 'PINKILAM' variety resulted from an open pollination of the cherry tree variety named 'RUBILAM' (U.S. Plant Pat. No. 23,798) which was used as the seed parent. Thus, the pollen parent is unknown.

The 'PINKILAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orienteles, France. More particularly, the plant was reproduced by grafting.

Every known type of grafting adapted to the cherry tree may be performed on the new tree. Especially, the type of grafting will depend on the grafting period and the propagation mode which is used by the nursery owner. Thus, the grafting period may be micrografting at any moment of the year if the grafting is performed in greenhouse, dormant eye shield budding in August or September, growing eye shield budding in June or July.

Compared to its female parent 'RUBILAM' variety (U.S. Plant Pat. No. 23,798), which is a red cherry tree, the new variety 'PINKILAM' is considered as a two-colored cherry tree.

Regarding the ripening period, the fruits of the new variety 'PINKILAM' ripen generally earlier than the fruits of the 'RUBILAM' variety, but it depends on the year. Generally, the fruits of 'PINKILAM' ripen 10 to 12 days before the fruits of 'RUBILAM'.

Moreover, the fruits of the new variety 'PINKILAM' are considered firmer than those of 'RUBILAM'.

Also, compared to the cherry tree named 'ROSALOLAM' (U.S. Plant Pat. No. 29,252), the ripening period is earlier, and the fruits produced by the new variety 'PINKILAM' ripen usually 10 to 12 days before the fruits of 'ROSALOLAM'.

Compared to the fruits produced by the cherry variety named 'BURLAT' (not patented), that show a weight of about 8 grams, the 'PINKILAM' variety produces fruits that are heavier, with a weight of approximately 11 to 12 grams, and the fruits of 'PINKILAM' have a bigger size.

Also, the variety named 'BURLAT' is a red cherry tree, whereas the new variety 'PINKILAM' is considered as a two-colored cherry tree.

Compared to 'FOLFER' cherry tree, which produces fruits having a sugary flavour, the 'PINKILAM' variety produces fruits having a semi-sweet flavour, very sugary.

SUMMARY OF THE NEW VARIETY

The new variety 'PINKILAM' produces fruits of important size, firm, with a semi-sweet flavor, low acidity, and a pinkish red color of skin on an orange cream background. The blooming period is medium for the variety, generally from the middle or end of March to beginning of April. The maturity period is considered early, and generally begins early in May or at the middle of the month, sometimes slightly later, in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
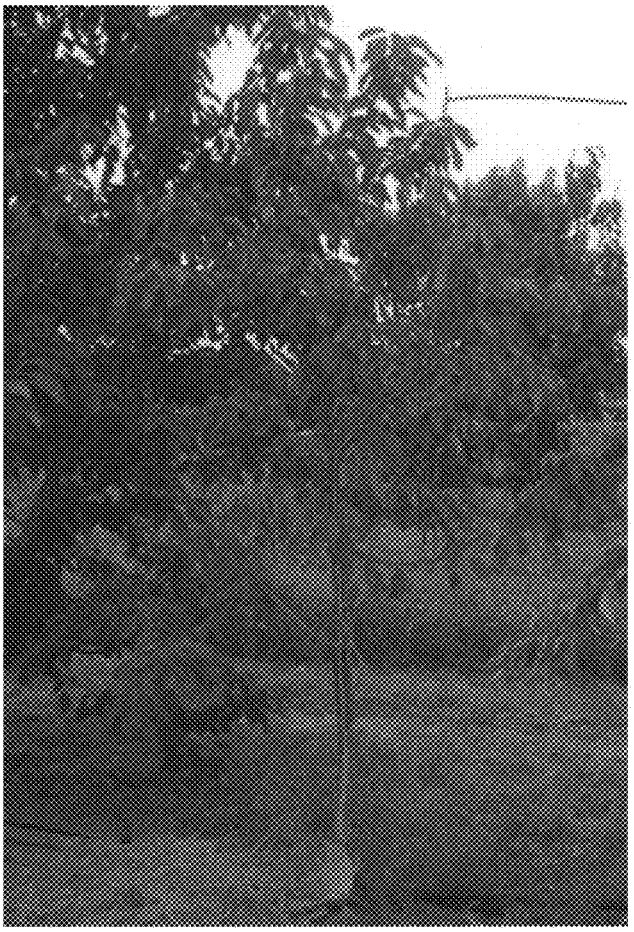
FIG. 1 is a color photograph which shows a view of a tree of the new variety in orchard.
Figure 2:
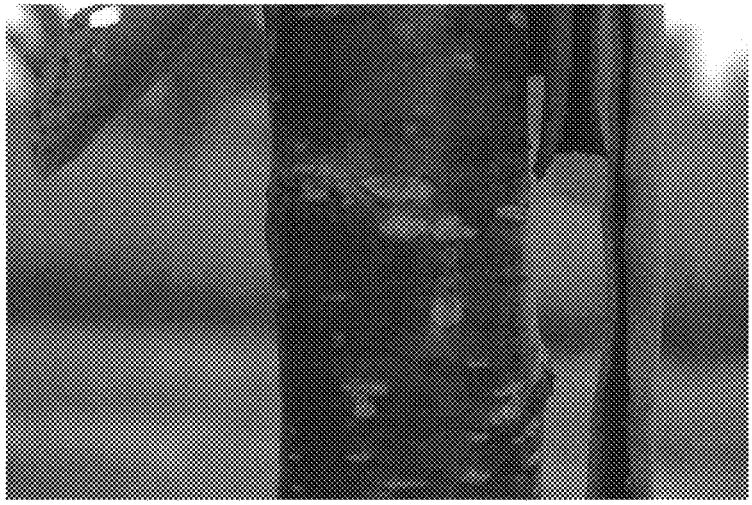
FIG. 2 is a color photograph that shows a close view of a portion of the trunk of the new variety.
Figure 3:
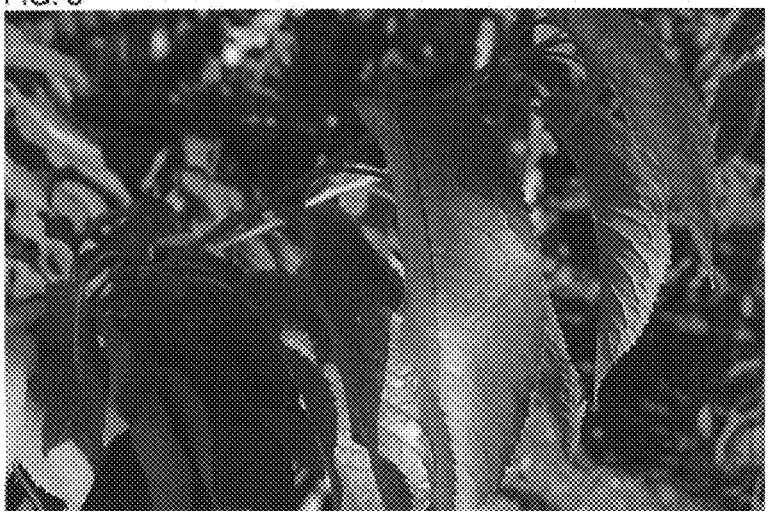
FIG. 3 is a color photograph which shows a close view of a branch for depicting the leaves in orchard.
Figure 4:
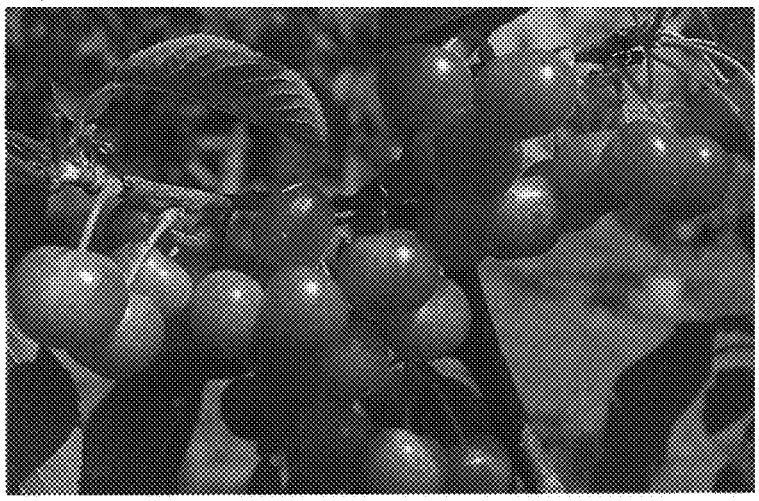
FIGS. 4 and 5 are both color photographs showing branches of the new variety, bearing fruits at ripening time.
Figure 5:
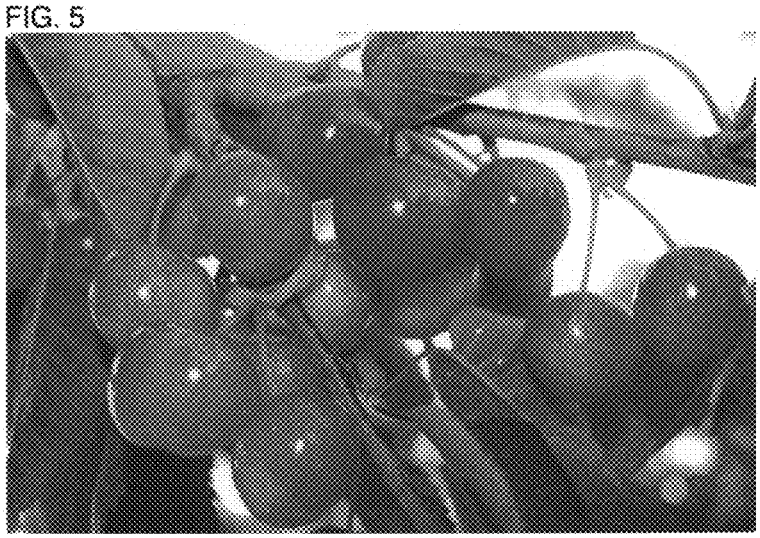
Figure 6:
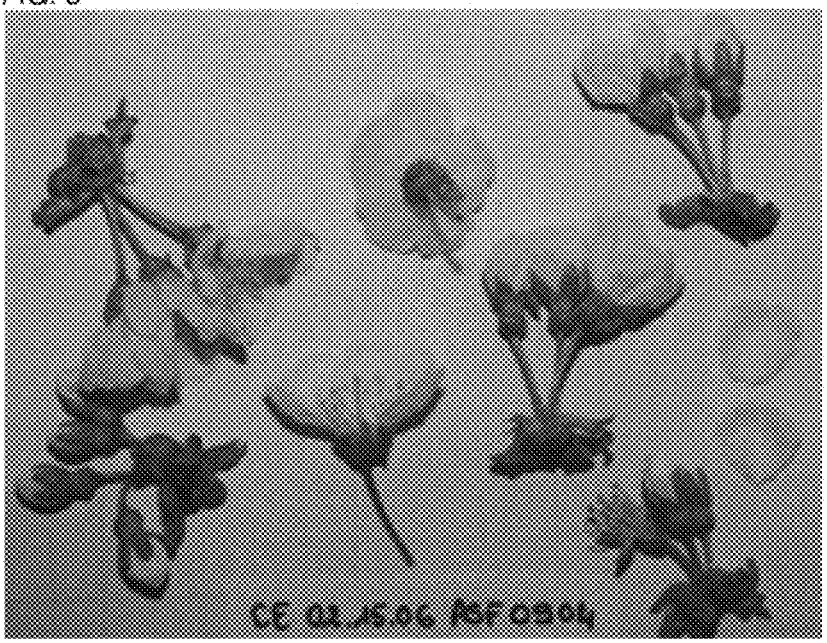
FIG. 6 shows typical white flowers of 'PINKILAM' variety at blooming for depicting the flower buds at different stages of development; and the reverse and side view of the flowers and the reproductive organs with petals removed, of the new variety, also referenced 'CE 02.15.06 ASF0904' on FIG. 6.
Figure 7:
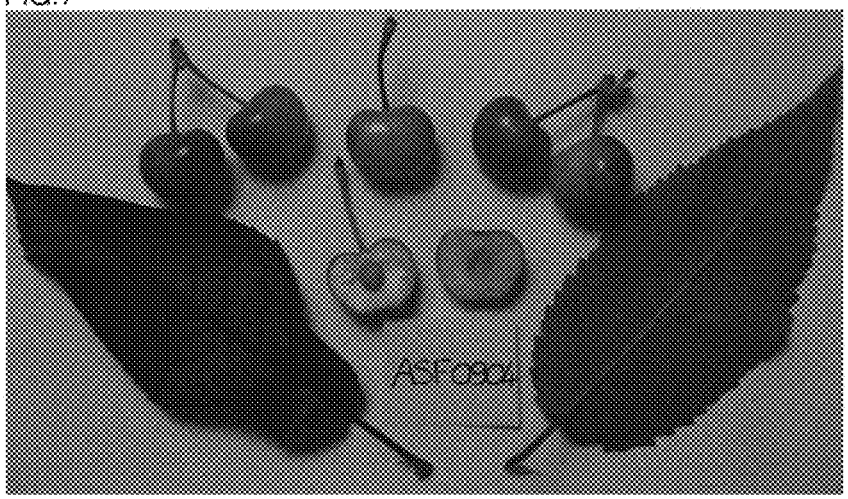
FIG. 7 is a color photograph which shows the upper and lower sides of leaves, five whole fruits of the new variety, and one fruit having been cut in a half, with the stone being left in one of the halves, for depicting the fruit flesh, the stone, and the stone cavity of the new variety, also referenced 'ASF0904' on FIG. 7.
Figure 8:
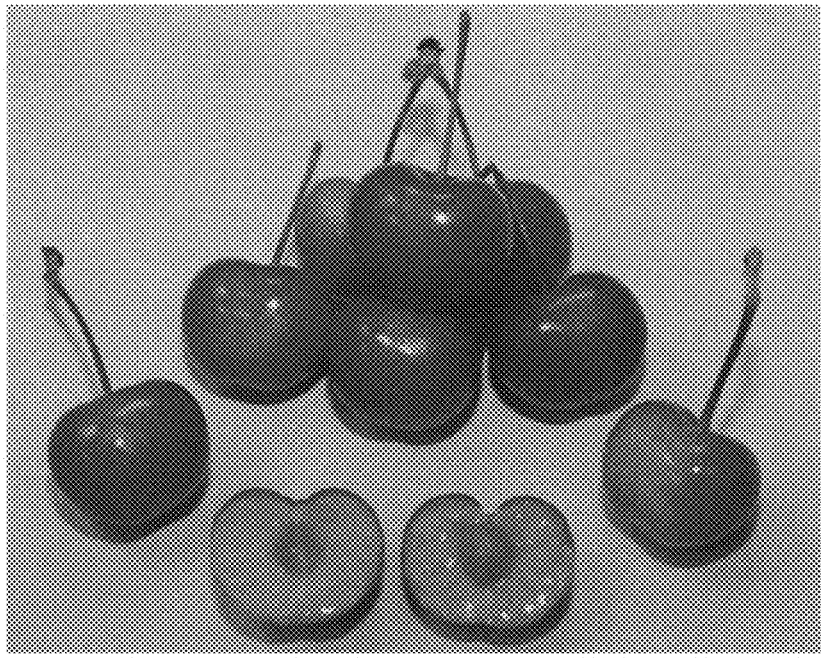
FIG. 8 is a color photograph that shows a close view of typical fruits of the new variety 'PINKILAM' at ripening time.
Figure 9:
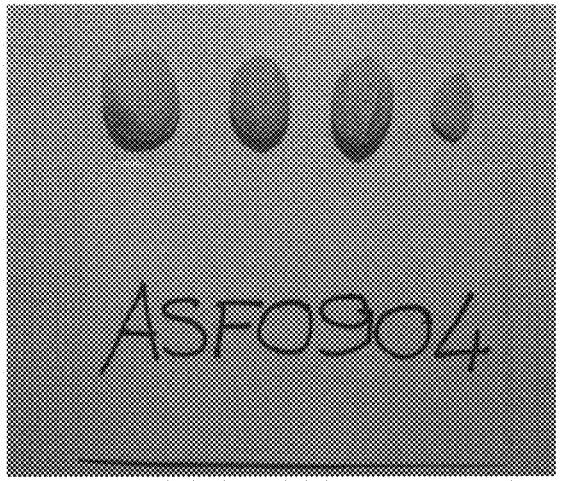
FIG. 9 is a color photograph showing different views of the stone and the kernel of the stone of the new variety, also referenced 'ASF0904' on FIG. 9.

The enclosed photographs show plants in their fifth growing season, except for the tree and trunk respectively illustrate on FIGS. 1 and 2, that have been observed in their third growing season.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. (Royal Horticultural Society) Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of semi-sweet cherry are a big fruit size with a two-colored skin considered pinkish red on an orange cream background. The color of fruit flesh is yellow to yellow orange. The fruit is very firm.

The time of beginning of flowering is medium and the time of beginning of fruit is considered early.

DETAILED DESCRIPTION

Referring more specifically to the pomological details of this new and distinct variety of cherry tree, the following has been observed on trees on their fifth growing season (fourth year of production) under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. (Royal Horticultural Society) Colour Chart 2001 (Fourth Edition) provided by The Royal Horticultural Society of Great Britain.

TREE

Generally: The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical, and the diameter is limited to 1 meter.

*Size.*—Medium to high as compared to other commercial sweet cherry cultivars. The tree size the first year was approximately 2.50 meters. The tree was pruned during each following dormant season to a height of approximately 2.50 meters. Current season's shoots growth could reach 0.60 to 0.80 meters. So, the tree size from the second year (second and next years) reached a final height of 3.10 to 3.30 meters. The mature branches have been pruned to a length of 30.0 centimeters in order to place nets on the trees.

*Spread.*—Approximately 2.0 meters with a cylindrical shape. The whole orchard was oriented to a central leader organization, with tree lines spaced of 4.0 meters and trees spaced of 1 meter in a same tree line.

*Vigor.*—Medium, tree growth reaching 0.60 to 0.80 meters the first growing season.

*Productivity.*—Good to very good productivity, every year. The new variety produces adequate fruit set annually on a regular basis. The number of the fruit set varies with the prevailing climatic conditions and cultivar practices employed during the bloom period and is therefore not distinctive of the present variety.

*Bearer.*—Very regular and quantitative. The extinction of the clusters of May improves the size and firmness of the fruit.

*Form.*—Semi-upright.

*Hardiness.*—Hardy in all stone fruit growing areas of France and especially where the chilling requirement is between 350 and 1200 hours. No injury with temperatures as low as −12° C. in winter. Good resistance to late frosts. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017 and 1017 hours in 2017-2018, showed a good behavior of the tree in all cases.

Trunk:

*Size.*—Medium. Approximately 55.0 millimeters above 20.0 centimeters from ground, on $5^{th}$ growing season.

*Bark texture.*—Smooth with reliefs due to the lenticels.

*Lenticels.*—High number of lenticels. The number of lenticels reaches 18 to 22 lenticels per 10 $cm^2$. At the $5^{th}$ growing season, lenticels are 1.5 to 2.0 millimeters in height and 4.0 to 8.0 millimeters in width.

*Lenticels color.*—Color of lenticels is brown (RHS GREYED ORANGE 166 C to RHS GREYED ORANGE 166 D).

*Bark color.*—Grey silver brown (RHS BROWN 200 B or RHS GREY 201 B).

Branches:

*Size.*—Medium for the branches at the $5^{th}$ growing season.

*Diameter.*—Average diameter of 20.0 to 30.0 millimeters.

*Surface texture.*—Smooth with lenticels, similar as bark texture. Wood that is several years old has no furrowed appearance.

*Color.*—Old growth is brown (RHS BROWN 200 B).

*Tree branching strength.*—Medium.

Current season shoots:

*Size.*—Medium for the new growth, between 60.0 and 80.0 centimeters.

*Diameter.*—Considered medium. Average diameter of about 5.3 millimeters.

*Surface texture.*—Smooth. Wood that is several years old has no furrowed appearance.

*Crotch angles.*—Primary branches are considered variable, but the crotch angles are generally between 55 degrees and 70 degrees from the vertical axis. This particular characteristic is not considered distinctive of the variety, however.

*Internode.*—Considered short. Generally from 62.0 millimeters to 72.0 millimeters length.

*Color.*—New growth is orange brown (RHS GREYED ORANGE 165 A).

LEAVES

Size: Medium to large for the species. Leaf measurements have been taken from vigorous, upright, current-season growth at approximately mid-shoot. The ratio leaf length/leaf width is 2.03.

Length: From 120.0 to 162.0 millimeters with leaf petiole. Average length with petiole 141.4 millimeters.

Width: From 64.0 to 79.0 millimeters. Average width 69.6 millimeters.

Leaf form in cross view: Concave.

Leaf form: Lanceolate to elliptic, large.

Apex: Acuminate.

Leaf base: Narrower than the rest of the leaves.

Leaf color:

*Upper leaf surface.*—Dark green (RHS GREEN GROUP 137 A or RHS GREEN GROUP 137 B).

*Lower surface.*—A lighter green than the upper leaf surface (RHS YELLOW GREEN GROUP 147 B).

*Leaf texture.*—Smooth. The lower surface is also smooth.

*Leaf venation.*—Pinnately veined.

Mid-vein:

*Color.*—Light green with a yellow touch (RHS YELLOW GREEN N144 A to RHS YELLOW GREEN N144 B) and evolves with maturity.

*Leaf margins.*—Undulating.

*Form.*—Considered dentate.

*Uniformity.*—Leaves are identical.

Leaf petioles:

*Size*—Considered medium.

*Length.*—About 30.0 to 37.0 millimeters.

*Diameter.*—About 2.0 millimeters.

*Color.*—Upper surface red (RHS GREYED PURPLE N 186 C). Lower surface brown (RHS GREYED BROWN 199 B).

*Ratio blade length/petiole length.*—Considered large. More or less 4.42.

Leaf glands:

*Size.*—Considered small. Their length is about 2.0 millimeters.

*Number.*—Generally 2.

*Type.*—Reniform.

*Color.*—Sometimes orange yellow to light red (RHS RED PURPLE 59 A), depending on the leaf age.

*Diameter.*—Approximately 1.0 to 1.5 millimeters.

Leaf stipules:

*Generally.*—No leaf stipules were observed.

FLOWERS

Flower buds:

*Generally.*—At pre-floral stage of development, the floral bunches are make up with 3 to 4 floral buds having a conic shape with a round tip. Their form is evolving until blooming, with variables dimensions. The floral bud shows a diameter of about 5.0 millimeters and are approximately 11.0 millimeters long. Then, just before blooming, floral buds have a diameter of about 10.0 millimeters wide and are approximately 20.0 millimeters long.

*Color.*—This characteristic is dependent upon the proximity to bloom. At pre-floral stage of development, the bottom of the flowers buds, or calyx, or flower receptacle, is of green or light green color at the upper surface (RHS YELLOW GREEN 144 A to RHS YELLOW GREEN 144 B) with purple pink areas (RHS GREYED RED GROUP 178 A to RHS GREYED RED GROUP 178 B). The lower surface of the calyx is also considered green or light green color (RHS YELLOW GREEN 144 B to RHS YELLOW GREEN 144 C) Above the calyx, the corolla, formed by petals, is generally pure white (RHS WHITE 155 D) on both upper and lower surfaces.

*Hardiness.*—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom.*—Generally late March. The first bloom was observed on March 19$^{th}$ until Mar. 30, 2011. Then, blooms took place respectively from March 30$^{th}$ until Apr. 6, 2012, them from April 3$^{rd}$ until Apr. 10, 2013, then from March 15$^{th}$ until Mar. 27, 2014, then from March 25$^{th}$ until Apr. 2, 2015, then from March 20$^{th}$ to Mar. 31, 2016, then from March 17$^{th}$ until Mar. 25, 2017 and then from April 1$^{st}$ until Apr. 9, 2018.

*Blooming time.*—Considered medium relative comparison to other commercial cherry cultivars grown in the Pyrénées-Orientales department, France. The date of full bloom is observed at the middle of the blooming period. The date of bloom varies slightly with climatic conditions and cultural practices.

*Blooming period.*—Average 7-12 days. This characteristic varies slightly with the prevailing climatic conditions.

*Flower type.*—The variety is considered to have a showy type flower.

*Flower size.*—Considered medium. Average diameter between 25.0 and 33.0 millimeters when totally opened.

*Bloom quantity.*—Considered abundant or very abundant.

*Flower bud frequency.*—Generally 3 to 4 flower buds appear per node.

Petal:

*Size.*—Considered medium for the species.

*Length.*—Generally between 18.0 and 20.0 millimeters.

*Width.*—Generally between 15.0 and 18.0 millimeters.

*Petal form.*—Large form, elliptic, narrower at the base and slightly pointed.

*Petal count.*—Nearly always 5.

*Petal texture.*—Both petal surfaces have a smooth texture.

*Petal margins.*—Smooth.

*Petal color.*—Pure white color (RHS WHITE 155 D) on both surfaces.

*Fragrance.*—Very soft.

*Arrangements of petals.*—Slightly overlapping.

Petal claw:

*Form.*—The claw is considered to have a conic form with a slightly rounded tip.

*Length.*—Approximately 7.0 millimeters.

*Width.*—Approximately 4.0 millimeters.

Petal apex:

*Generally.*—The petal apices are generally wide dome shaped.

Flower pedicel:

*Length.*—Considered medium to long and having an average length of approximately 18.0 to 20.0 millimeters.

*Diameter.*—Average 1.5 millimeter.

*Color.*—Green (RHS YELLOW GREEN 144 A to RHS YELLOW GREEN 144 B).

Calyx:

*Internal surface texture.*—Smooth.

*Color.*—The upper surface is of green or light green color (RHS YELLOW GREEN 144 A to RHS YELLOW GREEN 144 B) with purple pink areas (RHS GREYED RED GROUP 178 A to RHS GREYED RED GROUP 178 B). The lower surface of the calyx is also considered green or light green color (RHS YELLOW GREEN 144 B to RHS YELLOW GREEN 144 C).

Sepals:

*Surface texture.*—The outer and inner surfaces of the sepals have a smooth texture.

*Size.*—Usually considered medium.

*Length.*—Approximately 6.0 millimeters.

*Width.*—Approximately 4.0 millimeters.

*Shape.*—Elliptic shape.

*Color.*—The upper surface is green or light green color (RHS YELLOW GREEN 144 A to RHS YELLOW GREEN 144 B) with purple pink areas (RHS GREYED RED GROUP 178 A to RHS GREYED RED GROUP 178 B). The lower surface of the sepals is also considered green or light green color (RHS YELLOW GREEN 144 B to RHS YELLOW GREEN 144 C).

*Number of sepals.*—Generally 5, no overlapping.

*Sepal apex and margin descriptors.*—Elliptic in shape with a slightly rounder apex.

Stamens:

*Average number of stamens per flower.*—Between 42 and 48 stamens per flower.

*Stamen.*—Size compared to petals. The size of stamen is smaller than the size of petals.

Anthers:

*Length.*—Medium.

*Diameter.*—Approximately 1.0 millimeter.

*Form.*—Cardioid.

*Color.*—Yellow orange red color (RHS GREYED ORANGE 163 B to RHS GREYED ORANGE 163 C). The color evolves with flowering.

*Pollen production.*—Pollen is abundant and has a yellow color (RHS YELLOW ORANGE 17 B to RHS YELLOW ORANGE 17 C or RHS YELLOW ORANGE 9 A) that varies with maturity. The fertility has been checked and the 'PINKILAM' variety is not self-fertile (or self pollinating).

Filaments:

*Size.*—Variable in length, approximately between 5.0 and 12.0 millimeters in length, generally smaller than pistil's length.

*Color.*—Considered as white (RHS WHITE 155 D).

Pistil:

*Number.*—Usually 1.

*Length.*—Approximately from 16.0 to 17.0 millimeters including the ovary, that is longer than stamens length.

*Color.*—Considered very pale green (RHS YELLOW GREEN 149 B to RHS YELLOW GREEN 149 C). The color is evolving with flowering.

*Surface texture.*—Glabrous.

*Pubescence.*—Absent.

*Stigma.*—Approximately 1.1 millimeter in diameter, with an elliptic shape and a light green color (RHS YELLOW GREEN N 144 A to RHS YELLOW GREEN N 144 B).

*Ovary.*—Approximately 2.8 millimeters in height. The diameter of the ovary is about 1.9 millimeters. The color is considered green (RHS GREEN 143 A).

Type of reproduction: Pollination.

Pollinator: The following varieties are good pollinators: 'FERTILLE' cherry tree (not patented), 'DUROLAM ASF1612' cherry tree (not patented), 'REDLAM' cherry tree (U.S. Plant Pat. No. 29,317) and a selected cherry tree named 'ASF0902TH' (not patented).

FRUITS

Maturity when described: Firm at maturity.

Date of first picking. May 10, 2011. The date of picking varies slightly with climatic conditions.

Date of last picking. Last known picking times carry on from May 10$^{th}$ to May 25, 2011, then from May 28$^{th}$ to Jun. 7, 2012, then from May 26$^{th}$ to Jun. 2, 2013, then from May 5$^{th}$ to May 12, 2014, then from May 18$^{th}$ to May 24, 2015, then from May 20$^{th}$ to May 27, 2016, then from May 10$^{th}$ to May 16, 2017 and then from May 21$^{st}$ to May 28, 2018.

*Ripening period.*—Approximately 7 to 11 days.

Size:

*Generally.*—Considered large to very large, with a homogeneous size between them.

*Average cheek diameter.*—About 28.0 to 31.0 millimeters.

*Average axial diameter.*—About 23.0 to 25.0 millimeters.

*Typical weight.*—Generally about 9.8 to 11.5 grams. This characteristic is highly dependent upon the prevailing cultural practices, and therefore is not particularly distinctive of the variety.

Fruit form:

*Generally.*—Reniform.

*Fruit suture.*—Not marked.

Ventral surface:

*Form.*—Smooth.

*Apex.*—Round. Slightly in depression.

*Base.*—Slightly in depression.

*Stem cavity.*—Average depth of the stem cavity is about 2.0 to 3.0 millimeters. Average width is about 4.0 to 5.0 millimeters.

Fruit skin:

*Thickness.*—Considered smooth and medium to thin, and tenacious to the flesh depending on stage of maturity.

*Tenacity.*—Tenacious to flesh.

*Texture.*—Smooth.

*Taste.*—Sweet.

*Tendency to crack.*—None.

Color:

*Blush color.*—The color of the fruit is considered two colored. The fruit skin is colored on 50% of its surface in pinkish red (RHS RED GROUP 45 A or RHS RED GROUP 46 A) on an orange cream background (RHS YELLOW GROUP 11 A or RHS YELLOW GROUP 11 B or RHS YELLOW GROUP 11 C or RHS YELLOW GROUP 12 C).

*Fruit stem.*—Medium in length, approximately 33.0 to 38.0 millimeters.

*Diameter.*—Approximately 1.5 millimeters.

*Color.*—Light green (RHS GREEN GROUP 143 C or RHS GREEN GROUP 144 B).

*Lenticels.*—None.

Flesh:

*Ripens.*—Homogenous and regular.

*Texture.*—Very crunchy, luscious, juicy.

*Fibers.*—No fibers or with very few fibers.

*Firmness.*—Considered firm.

*Aroma.*—Pronounced aroma.

*Eating quality.*—Very good, very sweet, aromatic.

*Flavor.*—Semi-sweet, very sugared, aromatic. Low acidic level. Juicy and aromatic.

*Juice.*—Large amount, very juicy.

*Brix.*—Approximately 20.0 degrees, varies slightly with amount of fruit per tree and climatic conditions.

*Color of juice.*—From a cream color (RHS YELLOW GROUP 4 D) to an almost white color (RHS WHITE 155 D).

*Color of flesh.*—Cream (RHS YELLOW GROUP 11 B or RHS YELLOW GROUP 11 C or RHS YELLOW GROUP 11 D).

STONE

Type. Free stone to semi-freestone at fruits picking.

Size: Medium to small for the variety.

Length:. Average 10.0 millimeters.

Width: Average width 9.0 millimeters.

Diameter: Average diameter 7.0 millimeters.

Form: Round to slightly ovate.

Base: Generally round.

Apex: Round.

Stone cavity:. Medium with a form and dimensions corresponding to the stone's dimensions.

Stone surface:

*Surface texture.*—Smooth.

*Ridges.*—None, smooth.

*Tendency to split.*—Splitting is absent.

Ventral edge:

*Width.*—Very shallow, more or less 0.5 millimeter.

Dorsal edge:

*Shape.*—Full, with a slight relief.

*Stone color.*—The color of the dry stone is dark cream (RHS GREYED YELLOW 161 D).

*Tendency to split.*—None.

Kernel:

*Size.*—Medium.

*Length.*—About 8.0 millimeters.

*Width.*—About 5.0 millimeters.

*Thickness.*—About 3.0 millimeters.

*Form.*—Elliptic with a round-shaped apex and a pointed base.

*Pellicle.*—Not pubescent.

*Color.*—The kernel skin is dark cream (RHS GREYED YELLOW 162 B). The kernel and its embryo are mature at the time of fruit maturity.

Use: Dessert. Fresh products.

*Market.*—local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run and 'PINKILAM' variety seems to be low sensitive to pathologies, to rupture and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orienteles (66), France (FR).

We claim:

1. A new and distinct variety of cherry tree, substantially as illustrated and described, characterized by its precocious and important fruit set, its early ripening, its fruits and especially by its large to very large size, its two-colored fruit skin, its firmness, very good and semi-sweet flavor and eating quality; the fruit is further characterized by its good handling and storage qualities.

* * * * *